US009039672B2

(12) United States Patent
Wallen

(10) Patent No.: US 9,039,672 B2
(45) Date of Patent: May 26, 2015

(54) COUPLING COMPONENT FOR TRANSMITTING MEDICAL SUBSTANCES

(71) Applicant: Carmel Pharma AB, Göteborg (SE)

(72) Inventor: Claes Wallen, Sjömarken (SE)

(73) Assignee: Carmel Pharma AB, Gotteborg (SE)

( * ) Notice: Subject to any disclaimer, the term of this patent is extended or adjusted under 35 U.S.C. 154(b) by 0 days.

(21) Appl. No.: 13/974,380

(22) Filed: Aug. 23, 2013

(65) Prior Publication Data

US 2014/0000754 A1    Jan. 2, 2014

Related U.S. Application Data

(62) Division of application No. 11/030,098, filed on Jan. 7, 2005, now Pat. No. 8,545,475.

(30) Foreign Application Priority Data

Jul. 9, 2002    (SE) ...................................... 0202174

(51) Int. Cl.
*A61J 1/20*    (2006.01)
*A61J 1/10*    (2006.01)
(Continued)

(52) U.S. Cl.
CPC ............ *A61J 1/20* (2013.01); *A61J 2001/2027* (2013.01); *A61J 2001/1487* (2013.01); *A61J 2001/2041* (2013.01); *A61J 2001/2006* (2013.01); *A61J 2001/2055* (2013.01);
(Continued)

(58) Field of Classification Search
CPC ............. A61J 1/20; A61J 1/10; A61J 1/1475; A61J 1/1406; A61J 1/1443; A61J 1/2089; A61J 2001/14; A61J 2001/1443; A61J 2001/1475; A61J 2001/1481; A61J 2001/1487; A61J 2001/2003; A61J 2001/2006; A61J 2001/201; A61J 2001/2027; A61J 2001/2031; A61J 2001/2037; A61J 2001/2041; A61J 2001/2048; A61J 2001/2055; A61J 2001/2058; A61J 2001/2068; A61J 2001/2075; A61M 5/1409; A61M 5/162; A61M 39/14; A61M 39/221
See application file for complete search history.

(56) References Cited

U.S. PATENT DOCUMENTS 1,844,342 A    2/1932    Berman
2,010,417 A    8/1935    Schwab
(Continued)

FOREIGN PATENT DOCUMENTS

AU    200112863    5/2001
DE    2005519    10/1979
(Continued)

OTHER PUBLICATIONS

JP Appln No. 2003-583539, Office Action dated May 1, 2009, 3 pgs.
(Continued)

*Primary Examiner* — Adam Marcetich
(74) *Attorney, Agent, or Firm* — Servilla Whitney LLC

(57) ABSTRACT

A coupling component is disclosed for transmitting medical substances, comprising two channels for conveyance of medical substances in two substantially opposite directions and a means for releasable connection to a second coupling component having a further channel for creating a coupling. The connecting means is a thread. A method for conveying medical substances to and from a container is also disclosed.

6 Claims, 3 Drawing Sheets

Figure 1:
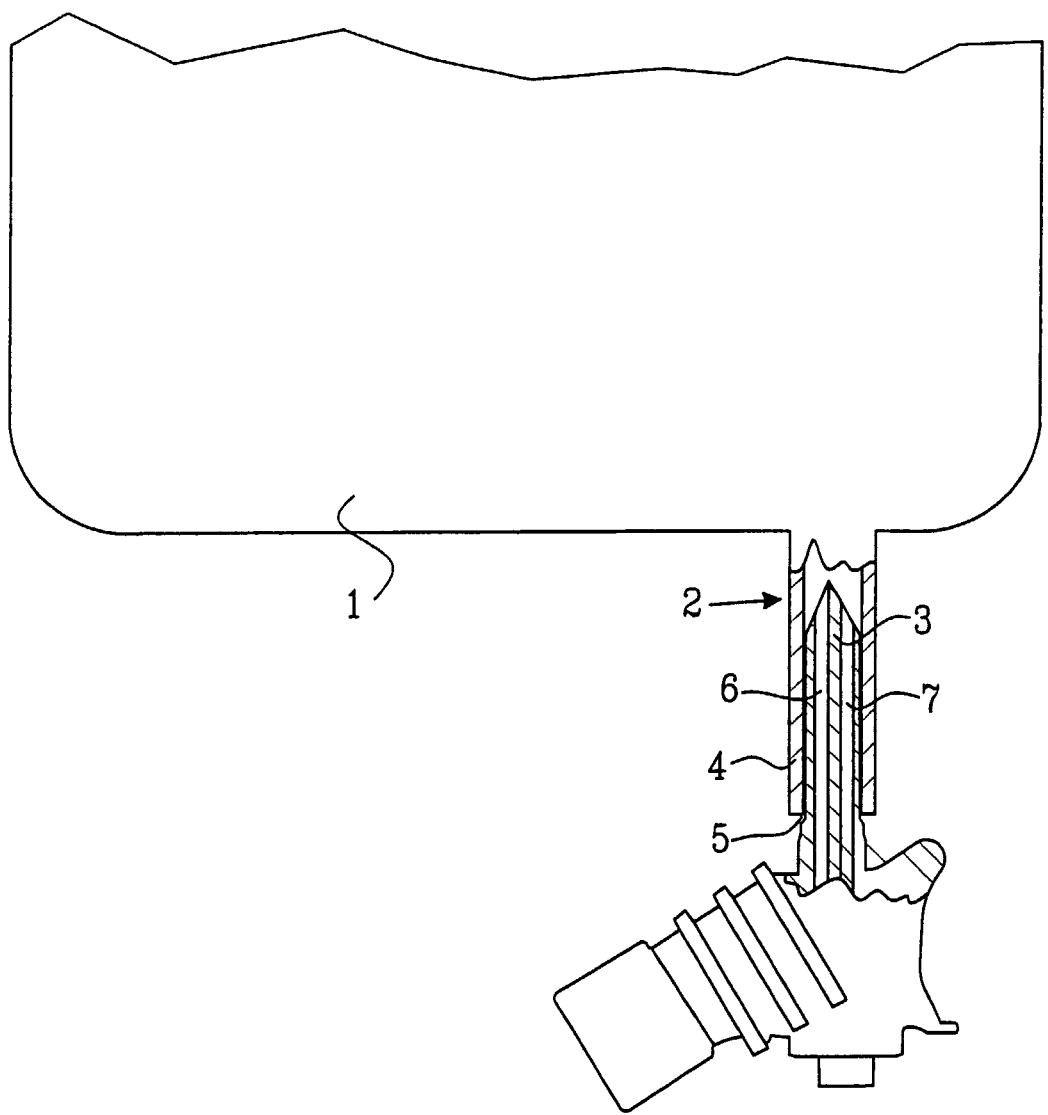

(51) Int. Cl.
*A61M 5/14* (2006.01)
*A61J 1/14* (2006.01)
*A61M 5/162* (2006.01)
*A61M 39/14* (2006.01)
*A61M 39/22* (2006.01)

(52) U.S. Cl.
CPC ........ *A61J2001/2003* (2013.01); *A61J 1/1406* (2013.01); *A61J 2001/201* (2013.01); *A61J 2001/1481* (2013.01); *A61J 2001/2048* (2013.01); *A61J 1/2089* (2013.01); *A61J 1/10* (2013.01); *A61J 1/1475* (2013.01); *A61M 5/1409* (2013.01); *A61M 5/162* (2013.01); *A61M 39/14* (2013.01); *A61M 39/221* (2013.01)

(56) References Cited

U.S. PATENT DOCUMENTS

| | | |
|---|---|---|
| 2,697,438 A | 12/1954 | Hickey |
| 2,717,599 A | 9/1955 | Huber |
| 3,064,651 A | 11/1962 | Henderson |
| 3,071,135 A | 1/1963 | Baldwin et al. |
| 3,308,822 A | 3/1967 | De Luca |
| 3,390,677 A | 7/1968 | Razimbaud |
| 3,448,740 A | 6/1969 | Figge |
| 3,788,320 A | 1/1974 | Dye |
| 3,822,700 A | 7/1974 | Pennington |
| 3,976,073 A | 8/1976 | Quick et al. |
| 3,986,508 A * | 10/1976 | Barrington .............. 604/411 |
| 4,161,178 A * | 7/1979 | Genese .............. 604/413 |
| 4,340,049 A | 7/1982 | Munsch |
| 4,479,989 A | 10/1984 | Mahal |
| 4,490,139 A | 12/1984 | Huizenga et al. |
| 4,516,967 A | 5/1985 | Kopfer |
| 4,564,054 A | 1/1986 | Gustavsson |
| 4,573,967 A | 3/1986 | Hargrove et al. |
| 4,576,211 A | 3/1986 | Valentini et al. |
| 4,581,016 A | 4/1986 | Gettig |
| 4,588,403 A | 5/1986 | Weiss et al. |
| 4,600,040 A | 7/1986 | Naslund |
| 4,629,455 A | 12/1986 | Kanno |
| 4,632,673 A | 12/1986 | Tiitola et al. |
| 4,657,541 A * | 4/1987 | Ichikawa et al. .............. 604/408 |
| 4,673,404 A | 6/1987 | Gustavsson |
| 4,737,150 A | 4/1988 | Baeumle et al. |
| 4,752,287 A | 6/1988 | Kurtz et al. |
| 4,768,568 A | 9/1988 | Fournier et al. |
| 4,792,329 A | 12/1988 | Schreuder |
| 4,822,340 A | 4/1989 | Kamstra |
| 4,826,492 A | 5/1989 | Magasi |
| 4,826,500 A | 5/1989 | Rautsola |
| 4,834,717 A | 5/1989 | Haber et al. |
| 4,842,585 A | 6/1989 | Witt |
| 4,850,978 A | 7/1989 | Dudar et al. |
| 4,864,717 A | 9/1989 | Baus, Jr. |
| 4,872,494 A | 10/1989 | Coccia |
| 4,878,897 A | 11/1989 | Katzin |
| 4,889,529 A | 12/1989 | Haindl |
| 4,898,209 A | 2/1990 | Zbed |
| 4,932,937 A | 6/1990 | Gustavsson et al. |
| 4,944,736 A | 7/1990 | Holtz |
| 4,964,855 A | 10/1990 | Todd et al. |
| 4,982,769 A | 1/1991 | Fournier et al. |
| 4,997,083 A | 3/1991 | Loretti et al. |
| 5,017,186 A | 5/1991 | Arnold |
| 5,041,105 A | 8/1991 | D'Alo et al. |
| 5,061,264 A | 10/1991 | Scarrow |
| 5,071,413 A | 12/1991 | Utterberg |
| 5,122,116 A | 6/1992 | Kriesel et al. |
| 5,122,123 A | 6/1992 | Vaillancourt |
| 5,137,524 A | 8/1992 | Lynn et al. |
| 5,158,554 A | 10/1992 | Jepson et al. |
| 5,176,673 A | 1/1993 | Marrucchi |
| 5,188,629 A | 2/1993 | Shimoda |
| 5,199,947 A | 4/1993 | Lopez et al. |
| 5,201,725 A | 4/1993 | Kling |
| 5,207,658 A | 5/1993 | Rosen et al. |
| 5,232,109 A | 8/1993 | Tirrell et al. |
| 5,254,097 A | 10/1993 | Schock et al. |
| 5,279,576 A | 1/1994 | Loo et al. |
| 5,279,583 A | 1/1994 | Shober, Jr. et al. |
| 5,279,605 A | 1/1994 | Karrasch et al. |
| 5,312,366 A | 5/1994 | Vailancourt |
| 5,328,480 A | 7/1994 | Melker et al. |
| 5,334,163 A | 8/1994 | Sinnett |
| 5,334,180 A | 8/1994 | Adolf et al. |
| 5,356,406 A | 10/1994 | Schraga |
| 5,385,545 A | 1/1995 | Kriesel et al. |
| 5,385,547 A | 1/1995 | Wong et al. |
| 5,389,085 A | 2/1995 | D'Alessio et al. |
| 5,405,326 A | 4/1995 | Haber et al. |
| 5,447,501 A | 9/1995 | Karlsson et al. |
| 5,456,675 A | 10/1995 | Wolbring et al. |
| 5,470,522 A | 11/1995 | Thome et al. |
| 5,478,328 A | 12/1995 | Silverman et al. |
| 5,478,337 A | 12/1995 | Okamoto et al. |
| 5,492,531 A | 2/1996 | Post et al. |
| 5,514,117 A | 5/1996 | Lynn |
| 5,515,871 A | 5/1996 | Bittner et al. |
| 5,536,259 A | 7/1996 | Utterberg |
| 5,575,780 A | 11/1996 | Saito |
| 5,593,028 A | 1/1997 | Haber et al. |
| 5,613,954 A | 3/1997 | Nelson et al. |
| 5,632,735 A | 5/1997 | Wyatt et al. |
| 5,647,845 A | 7/1997 | Haber et al. |
| 5,685,866 A | 11/1997 | Lopez |
| 5,735,841 A | 4/1998 | Bourguignon et al. |
| 5,752,942 A | 5/1998 | Doyle et al. |
| 5,755,712 A | 5/1998 | Szempruch et al. |
| 5,766,147 A | 6/1998 | Sancoff et al. |
| 5,766,211 A | 6/1998 | Wood et al. |
| 5,782,872 A | 7/1998 | Muller |
| 5,795,336 A | 8/1998 | Romano et al. |
| 5,817,083 A | 10/1998 | Shemesh et al. |
| 5,820,609 A | 10/1998 | Saito |
| 5,837,262 A | 11/1998 | Golubev et al. |
| 5,879,345 A | 3/1999 | Aneas |
| 5,897,526 A | 4/1999 | Vaillancourt |
| 5,984,899 A | 11/1999 | D'Alessio et al. |
| 6,063,068 A | 5/2000 | Fowles et al. |
| 6,070,623 A | 6/2000 | Aneas |
| 6,071,270 A | 6/2000 | Fowles et al. |
| 6,090,091 A | 7/2000 | Fowles et al. |
| 6,113,068 A | 9/2000 | Ryan |
| 6,113,583 A | 9/2000 | Fowles et al. |
| 6,142,446 A | 11/2000 | Leinsing |
| 6,146,362 A | 11/2000 | Turnbull et al. |
| 6,209,738 B1 | 4/2001 | Jansen et al. |
| 6,221,065 B1 | 4/2001 | Davis |
| 6,253,804 B1 | 7/2001 | Safabash |
| 6,258,078 B1 | 7/2001 | Thilly |
| 6,364,143 B1 | 4/2002 | Knierbein |
| 6,387,074 B1 | 5/2002 | Horppu et al. |
| 6,453,956 B2 | 9/2002 | Safabash |
| 6,471,674 B1 | 10/2002 | Emig et al. |
| 6,517,523 B1 | 2/2003 | Kaneko et al. |
| 6,537,263 B1 | 3/2003 | Aneas |
| 6,571,837 B2 | 6/2003 | Jansen et al. |
| 6,591,876 B2 | 7/2003 | Safabash |
| 6,644,367 B1 | 11/2003 | Savage et al. |
| 6,685,692 B2 | 2/2004 | Fathallah |
| 6,709,424 B1 * | 3/2004 | Knierbein .............. 604/411 |
| 6,715,520 B2 | 4/2004 | Andreasson et al. |
| 6,726,672 B1 | 4/2004 | Hanly et al. |
| 6,786,244 B1 | 9/2004 | Jones |
| 6,960,194 B2 | 11/2005 | Hommann et al. |
| 7,080,672 B2 | 7/2006 | Fournie et al. |
| 7,297,140 B2 | 11/2007 | Orlu et al. |
| 7,703,486 B2 | 4/2010 | Costanzo |
| 7,744,581 B2 | 6/2010 | Wallen et al. |
| 8,491,563 B2 * | 7/2013 | Wallen .............. 604/411 |
| 2001/0047154 A1 * | 11/2001 | Jepson et al. .............. 604/167.01 |
| 2002/0082586 A1 | 6/2002 | Finley et al. |
| 2002/0177819 A1 | 11/2002 | Barker et al. |

(56) References Cited

U.S. PATENT DOCUMENTS

| | | |
|---|---|---|
| 2003/0070726 A1 | 4/2003 | Andreasson et al. |
| 2003/0106610 A1 | 6/2003 | Roos et al. |
| 2003/0107628 A1 | 6/2003 | Fowles et al. |
| 2003/0177819 A1 | 9/2003 | Maale |
| 2003/0199846 A1 | 10/2003 | Fowles et al. |
| 2003/0233083 A1 | 12/2003 | Houwaert et al. |
| 2004/0116858 A1 | 6/2004 | Heinz et al. |
| 2004/0199139 A1 | 10/2004 | Fowles et al. |
| 2004/0215147 A1 | 10/2004 | Wessman et al. |
| 2005/0215977 A1 | 9/2005 | Uschold |
| 2006/0025747 A1 | 2/2006 | Sullivan et al. |
| 2006/0106360 A1 | 5/2006 | Wong |
| 2006/0111667 A1 | 5/2006 | Matsuura et al. |
| 2006/0157984 A1 | 7/2006 | Rome et al. |
| 2006/0186045 A1 | 8/2006 | Jensen et al. |
| 2007/0021725 A1 | 1/2007 | Villette |
| 2007/0060841 A1 | 3/2007 | Henshaw |
| 2007/0106244 A1 | 5/2007 | Mosler et al. |
| 2007/0179441 A1 | 8/2007 | Chevallier |
| 2007/0270759 A1 | 11/2007 | Pessin |
| 2008/0045919 A1 | 2/2008 | Jakob et al. |
| 2008/0103453 A1 | 5/2008 | Liversidge |
| 2008/0103485 A1 | 5/2008 | Kruger |
| 2008/0172039 A1 | 7/2008 | Raines |
| 2008/0223484 A1 | 9/2008 | Horppu |
| 2008/0287920 A1 | 11/2008 | Fangrow et al. |
| 2008/0312634 A1 | 12/2008 | Helmerson et al. |
| 2009/0254042 A1 | 10/2009 | Gratwohl et al. |

FOREIGN PATENT DOCUMENTS

| | | |
|---|---|---|
| EP | 0255025 | 2/1988 |
| EP | 0259582 | 3/1988 |
| EP | 0285424 | 5/1988 |
| EP | 0311787 | 4/1989 |
| EP | 0376629 | 7/1990 |
| EP | 0803267 | 10/1997 |
| EP | 0819442 | 1/1998 |
| EP | 0995453 | 4/2000 |
| EP | 1060730 | 12/2000 |
| EP | 1484073 | 12/2004 |
| EP | 1731128 | 12/2006 |
| FR | 2757405 | 6/1998 |
| FR | 2780878 | 1/2000 |
| GB | 1579065 | 11/1980 |
| JP | 4912690 | 5/1972 |
| JP | 288664 | 7/1990 |
| JP | 3030963 | 8/1996 |
| JP | 2000167022 | 6/2000 |
| JP | 2001505092 | 4/2001 |
| JP | 2001293085 | 10/2001 |
| TW | 482670 | 4/2002 |
| WO | WO-84/04672 | 12/1984 |
| WO | WO-84/04673 | 12/1984 |
| WO | WO-90/03536 | 4/1990 |
| WO | WO-9819724 | 5/1998 |
| WO | WO-99/27886 | 6/1999 |
| WO | WO-99/62578 | 12/1999 |
| WO | WO-00/05292 | 2/2000 |
| WO | WO-00/35517 | 6/2000 |
| WO | WO-01/80928 | 11/2001 |
| WO | WO-0202048 | 1/2002 |
| WO | WO-02/11794 | 2/2002 |
| WO | WO-02/064077 | 8/2002 |
| WO | WO-02/076540 | 10/2002 |
| WO | WO-2005/074860 | 8/2005 |
| WO | WO-2006/082350 | 8/2006 |
| WO | WO-2006/083333 | 8/2006 |
| WO | WO-2006/138184 | 12/2006 |
| WO | WO-2008/115102 | 9/2008 |

OTHER PUBLICATIONS

JP Office Action in Appln. 2003-577789, dated Feb. 24, 2009, 4 pgs.

PCT International Search Report in PCT/EP2008/067522, dated Aug. 12, 2009, 2 pgs.

PCT International Search Report in PCT/EP2008/067535, dated Oct. 13, 2009, 3 pgs.

Taiwan Search Report for Appln. 092106323, dated Mar. 21, 2003, 4 pgs.

\* cited by examiner

COUPLING COMPONENT FOR TRANSMITTING MEDICAL SUBSTANCES

CROSS-REFERENCE TO RELATED APPLICATIONS

This Application is a divisional of U.S. patent application Ser. No. 11/030,098 filed Jan. 7, 2005, now allowed, which is a 371 of Application No. PCT/SE2003/001193 filed Jul. 8, 2003 which claims priority from U.S. Provisional Application No. 60/394,288 filed Jul. 9, 2002 and Swedish Patent Application number 0202174-9, filed Jul. 9, 2002, the disclosures of which are hereby incorporated by reference in their entirety.

FIELD OF THE INVENTION AND PRIOR ART

The present invention relates to a coupling component for transmitting medical substances, comprising two channels for conveyance of medical substances in two substantially opposite directions and a means for releasable connection to a second coupling component having a further channel, for creating a coupling. Furthermore, the invention relates to a coupling for transmitting medical substances, comprising a first component having two channels for conveyance of medical substances in two substantially opposite directions, a second component having a further channel and a means for releasable connection of the first and the second component to each other for creating the coupling. The invention also relates to a method for conveyance of medical substances to and from a container, in which method a coupling component having two channels for conveyance of medical substances in two substantially opposite directions be connected to a second coupling component of a container, which second coupling component has a further channel.

The invention may be applied in different situations when medical substances are to be handled, but hereinafter the particular, but not in any way limiting for the invention, fields of application constituting a means for administration of fluids to/from infusion bags, which is desired in medical treatment for instance, will be described for illuminating purposes.

Infusion bags are used for intravenous delivery of fluids and medically effective substances to human beings and animals. For this reason, the infusion bag is provided with an outlet through which fluid may flow to a component connected to the patient, such as a cannula or the like, and further into the body of the patient. When preparing the fluids which are to be administrated to the body from the infusion bag, a usual method is that medically effective substances are supplied to a pre-sealed infusion bag which is filled with a transport fluid, such as a sodium chloride solution or a glucose solution. The preparation is performed by injecting the medically effective substance via an inlet into the bag.

For accomplishing the desired transportations of fluid a combined inlet and outlet of the infusion bag together with a coupling device which is denoted "spike" are often used. The spike has a first pointed end by means of which a membrane arranged in a narrow passage of the infusion bag, constituting inlet/outlet of the infusion bag, may be penetrated so that the infusion bag be opened towards two channels arranged in the spike when the spike is introduced in the inlet/outlet of the infusion bag. One of the channels is intended for conveyance of fluid in a direction from the infusion bag towards the patient and the other channel is intended for injection of medical substances into the infusion bag. In the other end of the spike are members arranged at the mouths of the channels for connection to other components, such as flexible tubes for conveyance of the fluid further to the patient and cannulas for the injection of medical substances to the infusion bag.

However, it has appeared that during certain extreme conditions there is a risk that the spike, which by insertion in the above mentioned narrow passage of the infusion bag is relatively loosely interconnected to the infusion bag, may unintentionally come loose from the infusion bag if the equipment is handled carelessly or by carelessness in connection with other treatment of the patient. The system of spike and infusion bag is depended of the friction between the infusion bag and the spike to prevent the spike from coming loose from the infusion bag. Furthermore, the spike has the disadvantage that leakage from the infusion bag to the environment may occur when the spike is introduced and the membrane is penetrated. In some cases the fluids which are to be administrated to the patient may be harmful to other persons than the patient who has been prescribed the treatment as a result of an indication of a specific decease. This is particularly the case when repeated long-term exposure is concerned, which can happened to medical staff when preparing and connecting infusion bags every day if the requisite security regulations are not fulfilled. A further disadvantage with the use of a spike which during the connection penetrates a membrane of the infusion bag for providing the fluid administration channels is that the connection step itself cannot be made in advance to later on enable conveyance of fluid from the infusion bag to a receiving unit connected to the spike, but the channels have to be opened instantaneously at the connecting moment.

THE OBJECT OF THE INVENTION AND SUMMARY OF THE INVENTION

One object of the invention is to provide a coupling component/coupling of the kind defined by way of introduction for transmitting medical substances, in which coupling component/coupling at least some of the discussed disadvantages of such previously known coupling devices has been reduced to a great extent.

This object is achieved by providing a coupling component. By a coupling component/coupling having the feature that the connecting means is a thread/a thread joint it is ensured that the coupling not be unintentionally uncoupled when the coupling is tension loaded. By means of the thread/ thread joint a coupling safe against tension load may be obtained at the same time as the connection may be accomplished quickly and safely in one simple operation. This implies that in the use of a device according to the invention, when an infusion bag is connected to a patient, an increased safety to the patient may be achieved at the same time as it is possible to deliver medical substances to the infusion bag and intravenously administrate fluid to the patient from the infusion bag. Furthermore the invention enables the use of other means, such as breakable fluid barrier plugs, for opening the infusion bag towards the channels and there is possible to ensure that leakage to the environment is prevented by tightening the thread joint before the infusion bag be opened towards the channels.

A further object of the invention is to provide a method of the kind defined by way of introduction, in which method a container and a coupling component, having two channels for conveyance of medical substances in two substantially opposite directions, may be connected to each other for conveyance of medical substances via the channels without the container being instantaneously opened towards the two channels.

This object is achieved by providing a method as described herein. Hereby the connection may be accomplished so as to later on enable conveyance of a medical substance from the container via one first of said two channels and/or conveyance of a medical substance to the container via the other of said two channels.

The invention also relates to an infusion bag and an infusion arrangement.

SHORT DESCRIPTION OF THE DRAWINGS

A description in greater detail of exemplifying embodiments of the invention will follow below with reference to the attached drawings.

Figure 2:
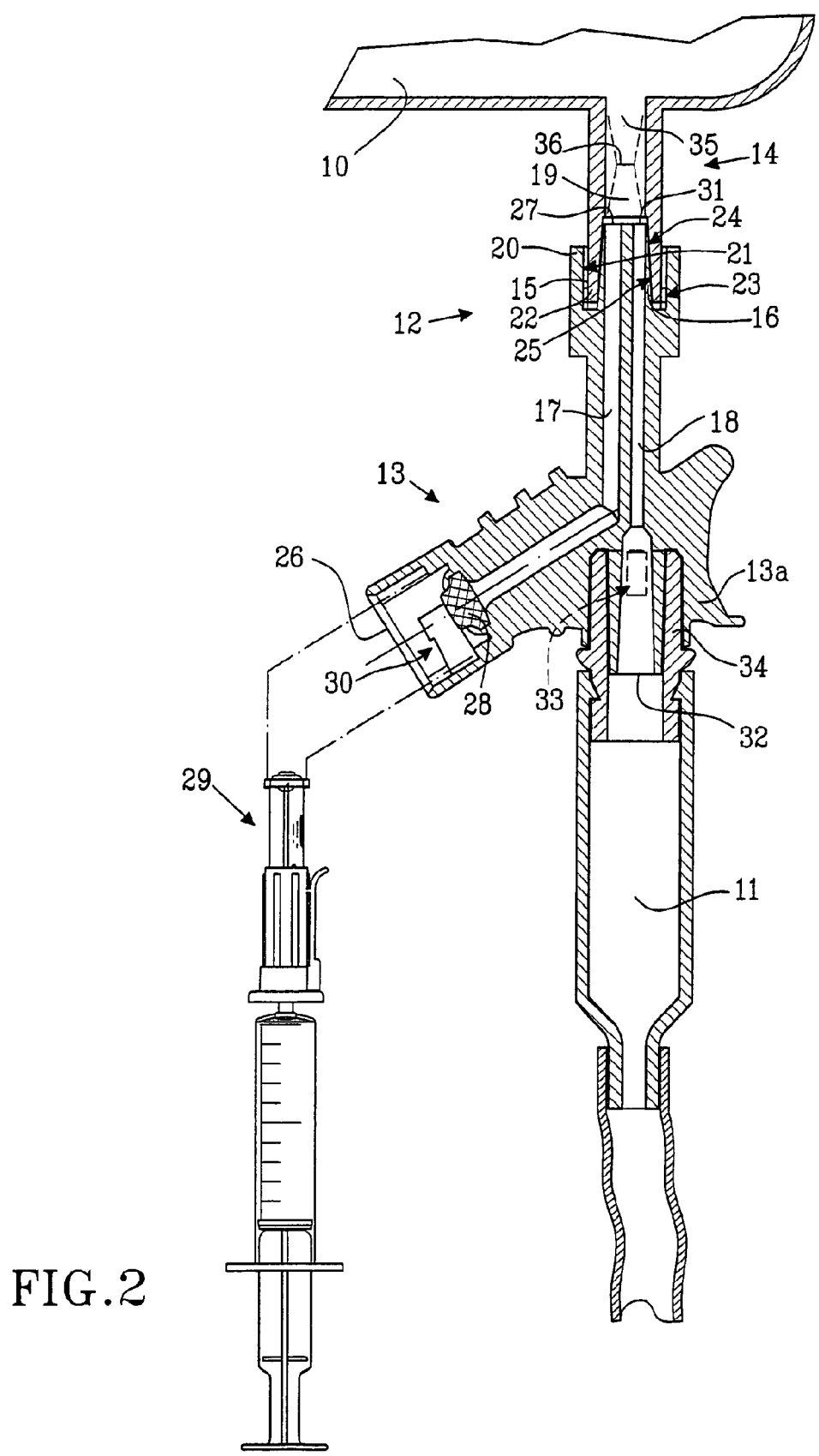
Figure 3:
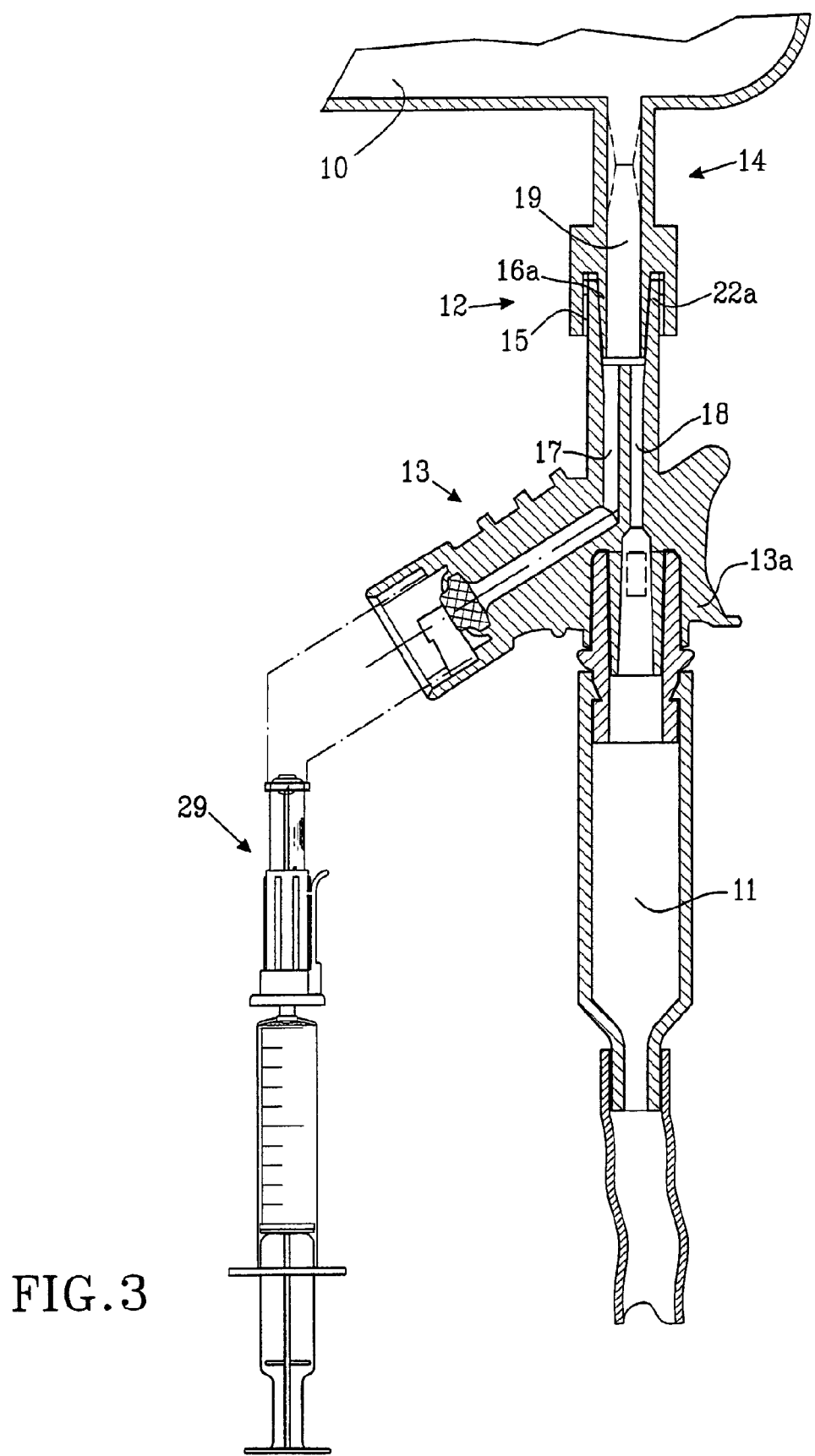

In the drawings:

FIG. 1 is a sectional view of an infusion bag and a spike according to prior art connected to the infusion bag, FIG. 2 is a sectional view of an infusion bag and a coupling according to the invention for transmitting medical substances, and FIG. 3 is a sectional view illustrating a variant of the coupling according to invention in FIG. 2.

DETAILED DESCRIPTION OF PREFERRED EMBODIMENTS OF THE INVENTION

In FIG. 1 an infusion bag 1 and a coupling device 2 of the type called spike according to prior art are illustrated. The coupling device 2 is provided with a pointed part 3 which is introducible in a part 4 which constitutes an inlet/outlet of the infusion bag 1. This part 4 of the infusion bag 1 is designed as a flexible tube with a circular cross-section corresponding to the cross-section of the pointed part 3 of the spike and has, before the introduction of the pointed part of the spike, a sealing membrane arranged at the mouth 5 thereof. In the introduction of the spike the pointed part 3 penetrates the membrane and the infusion bag 1 be opened towards two channels 6, 7 arranged in the spike. Thereafter, medical substances may be injected into the infusion bag 1 via one first 6 of the channels and fluid may be transported out from the bag via the other 7 of the channels to a receiving unit (not illustrated).

In FIG. 2 an infusion bag 10, a receiving unit 11 connected to the infusion bag and a coupling 12 according to the invention are illustrated. The coupling 12 comprises a first component 13, a second component 14 and a means 15 for releasable connection of the first 13 and second 14 components to each other for creating the coupling 12. The first component 13 comprises a male fitting 16 provided with two channels 17, 18 for conveyance of medical substances in two substantially opposite directions. One first channel 17 for injecting medical substances into the infusion bag 10 and one second channel 18 for conveyance of fluid out of the infusion bag 10 to the receiving unit 11, which may be for example a chamber or the like for intravenous treatment. The second component 14 is provided with a further channel 19 intended to be in communication with said two channels 17, 18 of the first component 13.

The connecting means 15 is a thread joint having the characteristic that said first 13 and second 14 components are locked against rectilinear movement relative to each other when being connected to each other and the coupling 12 is tension loaded. The first component 13 has a ring 20 partly enclosing the male fitting 16, which ring has a internal thread 21 constituting part of the thread joint. The ring 20 is concentrically arranged relative to the male fitting 16. The second component 14 comprises a female fitting 22 provided with said further channel 19 and an external thread 23 corresponding to said thread 21 of the ring 20 and constituting part of the thread joint. When the first and second components are to be connected to each other, i.e. when the first and the second components be screwed together, the male fitting 16 be introduced into the female fitting 22 to form a connection between said two channels 17, 18 of the first component 13 and the further channel 19 of the second component 14, which connection is sealed relative to the environment. For this purpose the male fitting 16 and/or female fitting 22 may be designed with a certain taper so that when the male fitting and the female fitting have been brought together a certain distance the outer surface 24 of the male fitting will abut against the inner surface 25 of the female fitting, and then further movement of the components in the introduction direction relative to each other is not longer possible and a sealing between the male fitting 16 and the female fitting 22 is obtained when tightening the thread joint 15.

Although the coupling component according to the invention, i.e. said first component, which has the both channels, is designed as a male fitting of the coupling in the illustrated example, in another embodiment it could be designed as a female fitting 22a of the coupling 12, such as illustrated in FIG. 3, and the other component, which is arranged on for example an infusion bag, would in such a case be designed as a corresponding male fitting 16a. Of course it is also possible to change places of the threads in comparison to the illustrated embodiment in FIG. 2, so that instead, the second component including the female fitting is provided with an internal thread and the first component including the male fitting is provided with an external thread. The threads may for example be arranged on rings such as described above.

Advantageously the design of the threads 21, 23, the male fitting 16 and the female fitting 22 may be in accordance with a so called luer fitting coupling such as in the illustrated embodiments.

The coupling component 13 according to the invention is provided with a port 26 for injection of a medical substance to the first of the channels 17 and further conveyance of this substance to the infusion bag 10. For this purpose, the first channel 17 has also an outlet 27 arranged at one end of the first coupling component 13 which exhibits the connecting means 15 and the second coupling component 14 has said further channel 19, which communicates with the first 17 and the second 18 channels, for introduction or removal of liquid to/from the infusion bag 10.

Within the frame of the invention the injection port 26 may be designed in different ways depending on which injection component is to be connected. In the illustrated embodiment the injection port 26 has a first flexible membrane 28 for co-operation with a second flexible membrane (not illustrated) arranged in an injection component 29 which is connectable to the injection port 26. The first membrane 28 is suitably air- and liquid proof and penetratable by an injection needle. To achieve a sealed connection of such a injection component 29 to the injection port 26, the injection port has a means 30 for holding said second flexible membrane with a pressure against said first flexible membrane 28. This holding means 30 may for example be constituted by a snap lock device, bayonet coupling or similar. The current pressure in question may suitably be chosen so that said first and second membranes are pressed together to a pressure exceeding the yield point of the both membranes, which implies that fluid cannot be pressed out through the contact surfaces of the membranes and a sealed connection is obtained.

If a pressure exceeding the yield point is applied the membranes will exhibit same properties at the compressed surfaces as in an arbitrary cross-section through the membranes, which implies that liquid cannot be pressed through the contact surfaces of the membranes. Such a characteristic may be obtained when the said first and second membranes has been pressed together to a pressure exceeding 150 kPa. Since the device risks to be destroyed if it is subjected to exceedingly large contact forces, the contact pressure should be restricted as much as possible. It has been proved in experiments that the sufficient sealing without any risk of failure is obtained with contact forces of up to 11, 1N, which corresponds to 656 kPA. Preferably, the contact pressure is within the interval 300-473 kPa.

At one end of the first coupling component 13, which end exhibits the connecting means 15 for establishing communication with the further channel 19 of the second coupling component 14 of the infusion bag 10, the second channel 18 has a inlet 31. Furthermore, the first coupling component 13 has in the other end thereof a port 32 which works as an outlet for the second channel 18. Within the frame of the invention the outlet port 32 may be designed in several different ways depending on which unit is to be connected to the outlet port. For example a snap coupling 33 may be used in combination with a friction joint for retaining a connection unit at the outlet port. In accordance with an variant thereof the entire coupling component 13, or at least the part 13a closest to the outlet port 32a of the coupling component 13, may be made of a first material and the connection unit 34 corresponding to the outlet port may be made of a second material. In this connection, materials having considerably different elasticity may be chosen, preferably so that the second material has a considerable higher elasticity than the first material for providing sufficient sealing action between the coupling component 13 and the connection unit 34 and at the same time achieve that the coupling component 13 having a lower elasticity has a high resistance against deformation.

In the extension of the further channel 19, i.e. in a combined inlet and outlet 35 of the infusion bag 10 a breakable fluid barrier plug 36 is arranged. In a state of not has been broken the fluid barrier plug 36 prevents in-flowing and out-flowing via the combined inlet and outlet 35 of the infusion bag 10 which implies that the infusion bag 10 is sealed. After connecting the infusion bag 10 to the coupling component 13 according to the invention, and eventually to other components, the fluid barrier plug 36 may be broken so that the combined inlet and outlet 35 of the infusion bag 10 be opened towards the both channels 17, 18 in the coupling component 13 according to the invention.

The method according to the invention comprises connecting of a coupling component 13 having two channels 17, 18 for conveyance of medical substances in two substantially opposite directions to a second coupling component 14 of a container 10, such as a infusion bag 10, which second coupling component has a further channel 19. After the coupling component 13 and the container 10 have been connected to each other, the container 10 be opened by means of a member 36, preferably in the form of a breakable fluid barrier plug or similar, which member is suitably arranged in a combine inlet and outlet 35 of the container 10, towards the both channels 17, 18 for enabling transportation of a medical substance to the container 10 via one first 17 of said two channels, and for enabling transportation of a medical substances from the container 10.

Preferably, the first 13 and the second 14 coupling components are connected to each other by a thread joint 15. By means of the thread joint 15 a male fitting 16 of the first component 13 may be brought into contact with a corresponding female fitting 22 of the second component 14 to form a connection sealed relative to the environment between said two channels 17, 18 and the further channel 19 of the second coupling component 14.

Then, the container 10 be opened towards 17, 18 by breaking the breakable fluid barrier plug 36. Thereafter, a medical substance may be injected to the container via one first 17 of said channels. Advantageously, the medical substance is injected by means of a component via a port arranged in the first coupling component which port has a first flexible membrane for co-operation with a second flexible membrane arranged in the injection component. Preferably, said second flexible membrane is held against said first flexible membrane with a pressure during the injection to prevent leakage and wastage during the injection. It has been proved that by holding said second flexible membrane against said first flexible membrane with a pressure exceeding the yield point of the first and second membranes it is ensured that the membranes fit tightly to each other in such away that fluid transportation between these membranes is prevented and thereby leakage to the environment is avoided. Parallel with the injection, the liquid state medical substance in the container may be transported via the second 18 of said two channels to a receiving unit.

It is stressed that the invention is not restricted to the exemplifying embodiments; rather within the scope of protection defined by the following claims, the invention may be varied in several ways once the idea of the invention is disclosed.

What is claimed is:

1. A method for conveyance of medical fluids to an infusion bag, comprising the steps of: connecting a first coupling component having two channels for conveyance of medical fluids in two opposite directions to a second coupling component of the infusion bag, wherein said first coupling component is provided with an opening for injection of a medical substance to a first of said two channels, wherein said opening is closed with a first piercable flexible membrane for abutting cooperation with a second flexible membrane of an injection component that is connectable to said opening, said second coupling component having a third channel with a lumen, said third channel is provided with a breakable fluid barrier that is arranged to remain intact during connection and upon complete engagement of the first coupling component to the second coupling component, wherein the breakable fluid barrier is contained within the lumen of the third channel; connecting the first coupling component and the second coupling component of the infusion bag allowing said second flexible membrane to be held against said first flexible membrane with a pressure exceeding the yield point of the first membrane and second membrane, and opening the infusion bag towards said two channels after the first coupling component and the infusion bag have been connected to each other, for enabling conveyance of a medical fluid into the infusion bag via one first of said two channels.

2. A method according to claim 1, whereby opening the infusion bag towards said two channels comprises breaking the breakable fluid barrier plug.

3. A method according to claim 1, further comprising opening the infusion bag towards said two channels by a member arranged in the infusion bag.

4. A method according to claim 1, further comprising injecting a medical fluid to the infusion bag via a first of said two channels.

5. A method according to claim 4, further comprising injecting the medical fluid via the opening arranged in the first coupling component.

6. A method according to claim 1, further comprising holding said second flexible membrane against said first flexible membrane with a pressure exceeding 150 kPa.

* * * * *